United States Patent

Krespan et al.

[11] Patent Number: 5,574,193
[45] Date of Patent: Nov. 12, 1996

[54] INITIATORS FOR TELOMERIZATION OF POLYFLUOROALKYL IODIDES WITH FLUOROOLEFINS

[75] Inventors: Carl G. Krespan; Viacheslav A. Petrov; Bruce E. Smart, all of Wilmington, Del.

[73] Assignee: E. I. Du Pont de Nemours and Company, Wilmington, Del.

[21] Appl. No.: 416,942

[22] Filed: Apr. 4, 1995

Related U.S. Application Data

[63] Continuation of Ser. No. 249,311, May 26, 1994, abandoned.

[51] Int. Cl.$^6$ .................................................. C07C 21/18
[52] U.S. Cl. ............................................................ 570/172
[58] Field of Search ................................................ 570/172

[56] References Cited

U.S. PATENT DOCUMENTS

| | | | |
|---|---|---|---|
| 3,132,185 | 5/1964 | Parsons | 260/653 |
| 3,234,294 | 2/1966 | Parsons | 260/653.1 |
| 3,404,189 | 10/1968 | Blochl | 260/653.1 |
| 4,067,916 | 1/1978 | Jaeger | 260/653.1 |
| 4,587,366 | 5/1986 | Werner | 570/172 |

FOREIGN PATENT DOCUMENTS

| | | | |
|---|---|---|---|
| 1301617 | 1/1973 | United Kingdom | C07C 17/28 |
| 1373320 | 11/1974 | United Kingdom | C07C 17/26 |
| 1535408 | 12/1978 | United Kingdom | C07C 17/28 |

OTHER PUBLICATIONS

Chen, J. *Fluor. Chem.*, 36(4), 483–489, 1987.
Hazeldine, R. N., *J. Chem. Soc.*, 3761–3768, 1953.
Fowler, R. D. et al, *Prep., Properties and Technology of Fluorine and Organic Fluoro Compounds*, Charles Slessler, Editor, McGraw–Hill, Chap. 26, 401–410, 1951.

*Primary Examiner*—Alan Siegel

[57] ABSTRACT

This invention relates to the telomerization of polyfluoroalkyl iodides with polyfluoroolefins in the presence of strong fluorooxidizer initiators. The products obtained are useful in the production of surfactants and oil repellants.

22 Claims, No Drawings

INITIATORS FOR TELOMERIZATION OF POLYFLUOROALKYL IODIDES WITH FLUOROOLEFINS

This is a continuation of application Ser. No. 08/249,311 filed May 26, 1994, now abandoned.

FIELD OF THE INVENTION

This invention relates to the telomerization of polyfluoroalkyl iodides with polyfluoroolefins in the presence of strong fluorooxidizer initiators. The polymers obtained are useful in surfactant manufacture.

TECHNICAL BACKGROUND

Telomeric perfluoroalkyl iodides are commercial products widely used for the preparation of a variety of valuable polyfluorinated compounds.

Various processes are known in the art for preparing perfluoroalkyl iodides based on the telomerization of lower perfluoroolefins (e.g., TFE) with fluoroalkyl iodides. A detailed description of the telomerization process is set forth in U.S. Pat. Nos. 3,234,294 and 3,132,185, which are incorporated herein by reference. The telomerization process takes place in the presence of an initiator. Some processes are initiated by peroxycompounds (Jap. Pat. 72-102032 and 72-102-031 10/12/1972, Ger. Pat. DE 2130378 1/27/1972, Fr. Pat. 2163444,08/31/1973, Ger. Pat. DE 2542496, 03/31/1977); some by metals (J. Fluor. Chem. 36(4), 483–489, 1987) or salts of some metals in combination with hydroxyalkylamines (U.S. Pat. No. 4,067,916, Jan. 10, 1978); others are thermally initiated (U.S. Pat. No. 3,404,189, 0/1/1968) or initiated by a mixture of $IF_5/SbF_5$ (U.S. 3,132,185, and U.S. Pat. No. 3,234,294, Feb. 8, 1966). These last two patent s teach the react ion of iodine, iodine pentafluoride and tetrafluoroethylene to produce perfluoroalkyl iodides, conducted in the presence of an antimony pentafluoride, antimony trifluoride or anhydrous stannous fluoride catalyst.

SUMMARY OF THE INVENTION

A process for preparing fluorinated alkyl iodides, which may also contain chlorine, comprising reacting a perfluoroalkyl iodide of lower molecular weight with a perfluoro olefin or monochlorofluoro olefin, at a temperature of 20° C. to 180° C. and at autogenous pressure, in the presence of a fluorooxidizer initiator. The initiator is selected from the group of metal fluorides or stable noble gas fluorides having an oxidation potential higher than that of mercuric fluoride. The process is optionally carried out in the presence of a solvent that is inert to the reaction.

DETAILS OF THE INVENTION

Strong fluorooxidizers are effective initiators for telomerization of perfluoroalkyl iodides with perfluoro olefins or monochlorofluoro olefins, such as tetrafluoroethylene (TFE) and chlorotrifluoroethylene (CTFE), to yield higher molecular weight iodides. These fluorooxidizer initiators work effectively in the telomerization process within a temperature range 20° C. to 180° C., preferably 20° C.–150° C., more preferably 50° C. to 150° C. The reaction results in formation of a mixture of telomeric perfluoroalkyl iodides.

By "telomerization" herein is meant a catalytic chemical reaction in which one or more molecules of a polymerizable substance combine with the fragments of another molecule (called telogen).

The usual product of the telomerization process described herein is a mixture of perfluoroalkyl iodides having a broad molecular weight distribution rather than a single product. Various methods are used to control the molecular weight distribution of product, including use of effective chain transfer agents, Hazeldine, J. Chem. Soc. 3761 (1953), and by performing the telomerization process rapidly in the gas phase (U.S. Pat. No. 3,404,189), which is incorporated herein by reference.

"Perfluoralkyl iodides" herein include the mono or diiodides and can be straight chain or branched, optionally containing chlorine and/or in-chain ether oxygen. These iodides are represented by the general formula $XCF_2CFYI$, wherein X is F, Cl , Br, $R_f$, or $OR_f$ and Y is F, Cl or $CF_3$ where $R_f$ is polyfluoroalkyl or a perfluoroalkyl group of up to 12 carbon atoms, linear or branched, optionally containing ether oxygen and/or a functional group such as I, $FSO_2$-, or $—C(O)OCH_3$. Preferred telogens include, but are not limited to, $CF_3CF_2I$, $CF_3CFClI$, $CF_2ClCF_2I$, $CF_2ClCFClI$, $CF_3CF_2CF_2CF_2I$, $(CF_3)_2CFI$, $ICF_2CF_2CF_2CF_2I$ and $CFOCF_2CF_2I$.

Perfluoro or chlorofluoroolefins for use in the process include but are not limited to $CF_2=CF_2$, $CF_2=CFC_1$, $CF_2=CFCF_3$, and $CF_2=CFOC_nF_{2n+1}$, where n is 1, 2, or 3.

The initiators useful in this invention are polyfluorides of metals in high valence states. Such metal fluorides are listed on page 403 of "Preparation, Properties and Technology of Fluorine and Organic Fluoro Compounds" by Slesser and Shram (McGraw-Hill, 1951), in the chapter by Fowler et al., entitled "Vapor-Phase Fluorination Using Metallic Fluorides Other Than Cobalt Trifluoride". Included therein are fluorides of chromium, manganese, cerium, lead, bismuth, cobalt and silver, all having oxidation potentials higher than that of mercuric fluoride. The fluorides of these metals in their highest valence states are recognized as being active fluorinating agents. Initiators for the present process include manganese trifluoride, cerium tetrafluoride, lead tetrafluoride, cobalt trifluoride, potassium and sodium tetrafluorocobaltates, and silver difluoride. Stable fluorides of noble gases, such as xenon difluoride, xenon tetrafluoride, xenon hexafluoride, $KrF_2$ or their salts EFn+MFm− may be also be used. Preferred initiators are $CoF_3$, $AgF_2$ and $XeF_2$; most preferred are $CoF_3$ and $AgF_2$. The above mentioned fluorides can be used in the pure state or on a support which is stable to the action of elemental fluorine at elevated temperature, i.e. conditions required for the reactivation of the initiator. Metal fluorides such as $CoF_2$, $CoF_3$, $MnF_3$, $MnF_2$, $CeF_3$, $AgF_2$, $Na_2CoF_4$ and $CeF_4$ can be supported on materials such as $AlF_3$, $CrF_3$, $ZnF_2$, $MgF_2$, $CaF_2$, graphites and fluorographites. Various methods of preparing supported metal fluorides useful in the present process are described, for example, in U.S. Pat. No. 5,300,710 and commonly assigned U.S. application Ser. No. 07/672,871. Also, metal fluoride initiators useful herein can be prepared by fluorinating materials prepared according to the method described in commonly assigned U.S. patent application Ser. No. 08/249,765 filed May 26, 1994, (Docket No. CR-9522), filed of even date herewith. These starting materials are a divalent metal fluoride phase (e.g. divalent metals are Mg, Co, Zn, Mn, and Cd) that is homogeneously dispersed with a trivalent metal fluoride phase (e.g. trivalent metals are Al, Ga, V and Cr, under the conditions described in Ser. No. 08/249, 765, filed May 26, 1994 (Docket No. CR-9522 ).

The proportion of initiator to alkyliodide is 0.0001 to 0.005 mole per mole of alkyliodide. The proportion of TFE used is 0.1–1 mole per mole of perfluoroalkyl iodide.

The reaction temperature is within the range of about 20° C.–180° C., preferably about 20° C. to 150° C., most preferably 50° C. to 150° C. Reaction times can vary from several minutes to several hours, depending on such variables as a initiator concentration, pressure and temperature.

The reaction can be carried out in the presence of a solvent that is inert to the reaction. Suitable solvents for the organic reactants include, but are not limited to $CF_2ClCFCl_2$, perfluorobutyltetrahydrofuran, perfluoro N-methylmorpholine and HFP cyclodimer.

Insoluble initiators, such as certain metal fluorides, e.g. $CoF_3$ and $MnF_3$, can be easily separated from the perfluoroalkyl iodide product by, for example, filtration and can be regenerated and reused. This ease of separating the initiators herein from the product presents an advantage over known initiator systems, such as $IF_5/SbF_5$ mixtures. The non-volatile metal fluorides can also be used in a flow system as a fixed bed.

The telomers produced herein are useful as intermediates to surfactants and oil repellants.

EXAMPLES

Example 1

400 mL Hastelloy shaker tube was charged with 500 mg of $XeF_2$, 100 g (0.29 mol) of perfluorobutyl iodide (PFBI) and 30 g (0.3 mol) of TFE and was kept on shaker at 20°–30° C. After 18 h at that temperature the gases were vented out at room temperature and the shaker tube was unloaded. Analysis of the crude product (100 g) by GC showed (in wt. %): $F(CF_2)_4I$ 67.1, $F(CF_2)_6I$ 8.5, $F(CF_2)_8I$ 6.9, $F(CF_2)_{10}I$ 5.6, $F(CF_2)_{12}I$ 4.0, $F(CF_2)_{14}I$ 2.2, $F(CF_2)_{16}$ 1.9, $F(CF_2)_{18}I$ 1.0 $F(CF_2)_{20}I$ and higher 2.8%, conversion of PFBI 33%.

Example 2

The reaction of Example 1 was repeated using 125 g (0.5 mol) of $C_2F_5I$ (PFEI), 20 g (0.2 tool) of tetrafluoroethylene (TFE) and 300 mg of $XeF_2$ (50° C., 18 h) . The shaker tube was unloaded, starting $C_2F_5I$ was distilled out from product on low temperature distillation column (91,5 g), the residue 18 g was dissolved in $CF_2ClCFCl_2$ and analyzed. GC analysis of the solution indicates presence of (in wt. %): $F(CF_2)_4I$ 22.4, $F(CF_2)_6I$ 17.9, $F(CF_2)_8I$ 19.4, $F(CF_2)_{10}I$ 13.4, $F(CF_2)_{12}I$ 10.5, $F(CF_2)_{14}I$ 7.5, $F(CF_2)_{16}I$ 4.5, $F(CF_2)_{18}I$ 13.0 $F(CF_2)_{20}I$ 1.5. Conversion of PFEI 25%, TFE 100%.

Example 3

Example 1 was repeated using different initiators in place of $XeF_2$. The results obtained are summarized in the Table 1.

TABLE 1

Fluorooxidizers as Initiators for Telomerization of TFE with Perfluoroalkyl Iodides

| No. | MF (mg) | $R_fI$ (g) | TFE (g) | T (°C.)* | Conv. (%)** $R_fI$ (TFE) |
|---|---|---|---|---|---|
| 1 | $CoF_3$ (300) | $C_2F_5I$ (100) | 20 | 20 | 46 |
| 2 | $CoF_3$ (500) | $C_2F_5I$ (45) | 10 | 70 | 25 (100) |
| 3 | $CoF_3$ (1000) | $C_4F_9I$ (100) | 20 | 50 | 33 (100) |
| 4 | $AgF_2$ (500) | $C_6F_{13}I$ (90) | 7 | 50 | 29 (100) |
| 5 | $MnF_3$ (200) | $C_2F_5I$ (50) | 10 | 50 | 18 |
| 6 | $CeF_4$ (300) | $C_4F_9I$ (50) | 10 | 50 | 6 |

*Reaction time 18 h
**In the above table, the last column represents the percent conversion of reagents $R_fI$ and TFE; $R_fI$(TFE).

Example 4

Example 1 was repeated using 200 mg of $CoF_3$, 50 g (0.17 mol) $(CF_3)_2CFI$ and 10 g (0.1 mol) of TFE (50° C., h). It was isolated 56 g of crude product, which was a mixture of 60% of starting iodide and 40% of higher oligomers. Starting iodide was distilled out, the residue was analyzed by GC (wt. % ): $C_5F_{11}I$ 25.2, $C_7F_{15}I$ 26.6, $C_9F_{19}I$ 19.2, $C_{11}F_{23}I$ 11.3, $C_{13}F_{27}I$ 7.1, $C_{15}F_{31}I$ 4.4, $C_{17}F_{35}I$ 2.8, $C_{19}$ and higher <3%. Conversion of $(CF_3)_2CFI$ was 33%, TFE 100%.

Example 5

Example 1 was repeated using 100 g (0.22 mol) of $I(CF_2)_4I$, 30 g (0.3 mol) of TFE and 300 mg of $CoF_3$ (50° C., 18 h). It was isolated 110 g of mixture containing 50% Of starting diiodide and 50% of telomers $I(CF_2CF_2)_nI$. Distillation in vacuum gave 90 g of material with b.p. 20°–100° C. at 200–1 mm Hg, which was mixture of $C_4$–$C_{10}$ oligomers. Sublimation in vacuum of solid residue (100°–200° C./1 mm Hg) gave additional 15 g of solid, mainly $C_{10}$–$C_{16}$ oligomers. Conversion of $I(CF_2CF_2)_2I$ was 42%, TFE 100%.

Example 6

Example 1 was repeated using 94 g (0.3 mol) of $CF_3OCF_2CF_2I$ 10 g (0.1 mol) TFE and 200 mg $CoF_3$ (50° C., 18 h) . 104 g of crude product was isolated, which was the mixture (GC, wt %) 76.5 $CF_3O$ $(CF_2)$ 2I, 7.7 $CF_3O$ $(CF_2)_4I$, 5.1 $CF_3O$ $(CF_2)_6I$, 3.8 $CF_3O$ $(CF_2)_8I$, 2.9 $CF_3O$ $(CF_2)_{10}I$, 2.2 $CF_{30}(CF_2)_{12}I$, 1.6 $CF_3O$ $(CF_2)_{14}I$. Conversion of starting iodide was 16%. All TFE was consumed.

Example 7

Example 1 was repeated using 74 g (0.3 mol) of PFBI, 10 g of TFE and 200 mg of $CoF_3$. After reaction 52 g of PFEI was recovered. Analysis of solution of telomers in cyclic dimer of HFP indicates presence of (wt. %) :$F(CF_2)_4I$ 20.6, $F(CF_2)_6I$ 20.7, $F(CF_2)_8I$ 16.1, $F(CF_2)_{10}I$ 12.2, $F(CF_2)_{12}I$ 9.6, $F(CF_2)_{14}I$ 7.5, $F(CF_2)_{16}$ 5.9, $F(CF_2)_{18}I$ 3.3, $F(CF_2)_{20}I$ 2.4 and higher 1.7%, conversion of PFEI was 28%, all TFE was consumed.

EXAMPLE 8

Preparation of Dispersed $CoF_3$ and $MnF_3$ Initiators

Homogeneously dispersed $CoF_2/AlF_3$ and $MnF_2/AlF_3$ in the form of 1.2 to 1.7 mm particles (or chunks or pellets) were used to prepare the initiators. These were prepared according to the process in co-pending application (Docket No.CR-9522). A thus prepared 4–5 g sample of $CoF_2/AlF_3$ (1:1 ratio) and a thus prepared 4–5 g sample of MnF$_2$/AlF$_3$ (1:1 ratio) were placed in Hastelloy reaction vessels, purged with N$_2$, pressured with 200–300 psi (1 ×10$^6$ –2 ×10$^6$ Pa) of a F$_2$/N$_2$ mixture (25:75) and were kept without shaking for 16h at 200° C. After fluorination, both samples showed a positive reaction with 10% solution of KI in water.

Example 9

(a) Example 1 was repeated using 74 g (0.3 mol) of PFEI, 10g of TFE and 500 mg of 1:1 CoF$_3$/AlF$_3$ initiator. The reaction mixture was kept on a shaker for 16h at 50° C. After reaction, PFEI was vented out, the residue (25g) was analyzed. Conversion of PFEI was 32%. All TFE was consumed.

(b) Example 1 was repeated using 90 g of C$_6$F$_{13}$I, 7 g TFE and 500 mg of 1:1 CoF$_3$/AlF$_3$ (80° C., 16h). The shaker tube was unloaded and the product (90g) was according to GC analysis, a mixture of 67% of starting material and 33% of telomeric perfluoroalkyl iodides. The conversion of C$_5$F$_{13}$I was 28%. All TFE was consumed.

After the experiment the granualated particles stayed intact and could be filtered easily to recover product.

Example 10

This example was carried out, as in Example 9, using 90 g of C$_6$F$_{13}$I, 7 g of TFE and 500 mg of 1:1 MnF$_3$/AlF$_3$. After 16 h at 100° C., 86 g of crude product was isolated. GC Analysis indicated that this product was a mixture of 87.3% starting material and 12.7% telomeric iodides. The conversion of C$_6$F$_{13}$I was 16.6%.

After the experiment the granualated particles stayed intact and could be filtered easily to recover product.

What is claimed is:

1. A process for preparing fluorinated alkyl iodide telomers, which may also contain chlorine, consisting of telomerizing a starting perfluoroalkyl iodide with a terminally unsaturated perfluoro olefin or monochlorofluoro olefin, at a temperature of about 20° C. to 180° C. and at autogenous pressure, in the presence of a metal fluoride initiator, wherein the metal fluoride is a more powerful oxidizer than mercuric fluoride, wherein the initiator is selected from the group consisting of CrF$_3$, CrF$_4$, CrF$_5$, MnF$_3$, MnF$_4$, CeF$_4$, PbF$_4$, BiF$_5$, CoF$_3$, KCoF$_4$, NaCoF$_4$, AgF$_2$, and VF$_5$ and stable fluorides of noble gases and in the presence of a solvent selected from the group consisting of CFCl$_2$CF$_2$Cl, perflourobutyltetrahydrofuran and HFP cyclodimer or in the absence of added solvent.

2. The process of claim 1 wherein the starting perfluoroalkyl iodide is selected from the group consisting of CF$_3$CF$_2$I, CF$_3$CFClI, CF$_2$C$_1$CF$_2$I, ClCF$_2$CFClI CF$_3$CF$_2$CF$_2$CF$_2$I, (CF$_3$)$_2$CFI, CF$_2$ClCFClI and ICF$_2$CF$_2$CF$_2$CF$_2$I.

3. The process of claim 1 wherein the fluoroolefin in is selected from the group consisting of CF$_2$=CF$_2$, CF$_2$=CFCl, CF$_2$=CFCF$_3$ and CF$_2$=CFOC$_n$F$_{2n+1}$I where n is 1, 2, or 3.

4. The process of claim 1 wherein the initiator is a fluoride selected from the group consisting of CoF$_3$, MnF$_3$, XeF$_2$, CeF$_4$, CrF$_3$, and AgF$_2$.

5. The process of claim 4 wherein the initiator is CoF$_3$.

6. The process of claim 4 wherein the initiator i s AgF$_2$.

7. The process of claim 4 wherein the initiator is supported on a material stable to the action of elemental fluorine at elevated temperatures.

8. The process of claim 7 wherein the support consists of material selected from the group consisting of AlF$_3$, ZnF$_2$, MgF$_2$, CaF$_2$, and graphite.

9. The process of claim wherein the initiator is in the form of a dispersion produced by fluorinating a first metal fluoride homogeneously dispersed in a second material selected from the group consisting of AlF$_3$, CrF$_3$, ZnF$_2$, MgF$_2$, CaF$_2$, and fluorinated graphite.

10. The process of claim 1 wherein the process is carried out in the presence of a solvent L selected from the group consisting of CFCl$_2$CF$_2$Cl , perfluorobutyltetrahydrofuran and HFP cyclodimer.

11. The process according to claim 1 wherein the process is carried out at a temperature of between 50° C. and 150° C.

12. The process according to claim 1 wherein the pressure is about atmospheric pressure.

13. The process according to claim 1 wherein the pressure is above atmospheric pressure.

14. The process of claim 1 wherein the proportion of initiator to perfluoroalkyl iodide is 0.0001–0.005 mole per mole of perfluoroalkyl iodide.

15. The process of claim 1 wherein the proportion of perfluoroolefin used is 0.1–1 mole per mole of perfluoroalkyl iodide.

16. Process of claim 1 conducted in the presence of a metal fluoride initiator bed in a flow system.

17. Process of claim 1 conducted in the presence of a metal fluoride initiator bed in a flow system wherein the initiator is supported on a material stable to elemental fluorine.

18. Process of claim 17 wherein the material stable to elemental fluorine is CoF$_3$.

19. The process of claim 17 conducted within a temperature range of 50° C. to 180° C.

20. The Process of claim 16 wherein the intiator is a metal fluoride dispersion produced by fluorinating a fluoride of a divalent metal homogeneously dispersed with a fluoride of a trivalent metal.

21. The process of claim 1 wherein the initiator is CoF$_3$.

22. The process of claim 21 wherein the initiator is CoF$_3$ and where CoF$_2$ is also present.

* * * * *